United States Patent
Laane et al.

(10) Patent No.: US 9,756,861 B2
(45) Date of Patent: *Sep. 12, 2017

(54) MICRO-COLLOIDAL SILICIC ACID / BORIC ACID COMPOSITION AND A METHOD OF PREPARING A BIOENHANCING SOLUTION AND POWDER

(71) Applicant: Barlaa B.V., Muiden (NL)

(72) Inventors: Henk Maarten Laane, Muiden (NL); Walter Ferdinand Witterland, Leusden (NL)

(73) Assignee: Barlaa B.V., Muiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,703

(22) Filed: Dec. 4, 2015

(65) Prior Publication Data

US 2016/0088845 A1   Mar. 31, 2016

Related U.S. Application Data

(63) Continuation of application No. 14/106,625, filed on Dec. 13, 2013, now Pat. No. 9,215,890, which is a continuation of application No. 13/514,938, filed as application No. PCT/NL2010/050831 on Dec. 8, 2010, now abandoned.

(30) Foreign Application Priority Data

Dec. 9, 2009   (IN) ............................ 2202/CHE/2009

(51) Int. Cl.
*A01N 59/20* (2006.01)
*A01N 59/00* (2006.01)
*A01N 59/14* (2006.01)
*A61K 31/69* (2006.01)
*A61K 31/695* (2006.01)
*C05D 9/02* (2006.01)
*C05G 3/00* (2006.01)
*A61K 33/00* (2006.01)
*A61K 33/04* (2006.01)
*A61K 33/22* (2006.01)
*A61K 33/30* (2006.01)
*A61K 33/34* (2006.01)
*A01N 59/02* (2006.01)
*A01N 59/16* (2006.01)
*A61K 33/24* (2006.01)
*A23L 33/10* (2016.01)
*A23L 33/16* (2016.01)

(52) U.S. Cl.
CPC ............. *A01N 59/20* (2013.01); *A01N 59/00* (2013.01); *A01N 59/02* (2013.01); *A01N 59/14* (2013.01); *A01N 59/16* (2013.01); *A23L 33/10* (2016.08); *A23L 33/16* (2016.08); *A61K 31/69* (2013.01); *A61K 31/695* (2013.01); *A61K 33/00* (2013.01); *A61K 33/04* (2013.01); *A61K 33/22* (2013.01); *A61K 33/24* (2013.01); *A61K 33/30* (2013.01); *A61K 33/34* (2013.01); *C05D 9/02* (2013.01); *C05G 3/007* (2013.01); *A23V 2002/00* (2013.01)

(58) Field of Classification Search
CPC ........ A01N 59/00; A01N 59/14; A01N 25/02; A01N 25/12; A01N 25/22; A61K 31/69; A61K 31/695; C05D 9/02; C05G 3/007
See application file for complete search history.

(56) References Cited

U.S. PATENT DOCUMENTS

| 2006/0178268 | A1  | 8/2006 | Kros |
|---|---|---|---|
| 2011/0064798 | A1* | 3/2011 | Suvee .................... A61K 8/044 424/451 |

FOREIGN PATENT DOCUMENTS

| WO | WO-02/078865 A1 | 10/2002 |
| WO | WO-03/101915 A1 | 12/2003 |
| WO | WO-2009/127256 A1 | 10/2009 |
| WO | WO-2009/144087 A2 | 12/2009 |

OTHER PUBLICATIONS

Bengsch E., "Effects of Simultaneous Supply of Silicon and Boron on Plant Growth and on Herbicide Toxicity," (1989) Verlag Zeitschrift Naturf. D-7400 Tübingen 0341 013 0382/89/0900-0781.
Bengsch E., "Reduction in Symptom Expression of Belladonna Mottle Virus Infection on Tobacco Plants by Boron Supply and the Antagonistic Action of Silicon," Verlag Zeits Naturf., 1989, D-7400 Tübingen 0341 013 0382/89/0900-0777.
Epstein, E., "Silicon," Ann Rev Plant Physiol. Plant. Mol. Biol., 1999, vol. 50, pp. 641-664.
International Search Report for PCT/NL2010/050831—mailed May 10, 2011.

(Continued)

*Primary Examiner* — Robert Cabral
(74) *Attorney, Agent, or Firm* — Gilberto M. Villacorta; Sunit Talapatra; Foley & Lardner LLP

(57) ABSTRACT

The present invention provides a composition comprising an acidified aqueous solution of (1) micro colloidal silicic acid, (2) boric acid, and (3) a water absorbing additive, having a pH value of equal to or less than 1, wherein the micro colloidal silicic acid has particle sizes in the range of 1-8 nm, especially in the range of 1.5-6 nm. The invention also provides a particulate product obtainable by the method according to claim 18, wherein the particles comprise (1) silicic acid, (2) boric acid, and (3) the water absorbing additive, and wherein at least 90% of the particles in the particulate product have particle sizes in the range of 0.3-5 μm.

8 Claims, No Drawings

(56) References Cited

OTHER PUBLICATIONS

Van Dyck, Kristien et al. "Bioavailability of silicon from food and food supplements" Fresenius J Anal Chem, vol. 363, 1999, pp. 541-544, XP002633342.
Yamaguchi, H. "Silicic acid/boric acid complexes as ecologically friendly wood preservatives", Forest Products Journal, Jan. 2005, 55(1); 88-92.

* cited by examiner

MICRO-COLLOIDAL SILICIC ACID / BORIC ACID COMPOSITION AND A METHOD OF PREPARING A BIOENHANCING SOLUTION AND POWDER

CROSS-REFERENCE TO RELATED PATENT APPLICATIONS

This application is a Continuation of U.S. application Ser. No. 14/106,625, filed Dec. 13, 2013, which is a Continuation of U.S. application Ser. No. 13/514,938, filed as the National Stage application of PCT/NL2010/050831, filed Dec. 8, 2010, which claims priority from Indian Patent Application No. 2202/CHE/2009, filed Dec. 9, 2009. These applications are herein incorporated by reference in their entirety.

FIELD OF THE INVENTION

The invention relates to stable aqueous solutions and powders containing bioavailable and bioactive silicon and boron that can be used to enhance and strengthen plants and trees, or as food, food additives, or as creams (gels, a.o.), to improve the health of humans and/or animals.

The invention is also related to the preparation of stable solutions and powders containing bio-available silicon and boron and optionally other elements like copper, molybdenum, selenium, zinc, compounds like amino acids, humic and fulvic acids and (other) nutrients.

BACKGROUND OF THE INVENTION

Silicon is an essential nutrient for plants. In modern agriculture systems however, the nutrient solutions are mostly deficient in bioavailable silicon.

As is known (Epstein, E (1999). Silicon. Ann Rev Plant Physiol. Plant Mol. Biol. 50:641-64.), silicon is beneficial for hardening the roots of plants, and is also beneficial or even essential for good plant growth and disease resistance. Leafs are strengthened through an outer opal layer, built of silicic acid polymers acting as a mechanical barrier. Silicon also connects plant substances such as sugars, proteins or phenolic compounds which are present in all kinds of plant fibres. Mycelia of fungi cannot penetrate the plant anymore: Silicon is essential against biotic and abiotic stresses: it increases the yield, induces resistance to stress, controls diseases and pests, reduces toxicity of certain minerals as manganese and aluminium, increases tolerance to freeze calamities, regulates water consumption and improves leaf erectness, resulting in photosynthesis enhancement.

Boron is also an essential nutrient for plants. The combination of boron and silicon show synergistic or antagonistic effects on plant growth and disease resistance, dependant of their concentrations (Bengsch, E(1989). Reduction in symptom Expression of Belladonna Mottle Virus Infection on Tobacco Plants by Boron Supply and the Antagonistic Action of Silicon: Verlag Zeits Naturf. D-7400 Tubingen 0341-0382/89/0900-0777 and Bengsch, E(1989). Effects of simultaneous supply of Silicon and Boron on Plant Growth and on Herbicide toxicity: Verlag Zeitschrift Naturf. D-7400 Tubingen 0341-0382/89/0900-0781). The right concentrations of both nutrients induce synergistic effects on the increase of yield and an increased resistance to diseases and pests.

SUMMARY OF THE INVENTION

Silicon is an essential nutrient for plants and may be present as small sized silicic acid in soil, mineral, river and ocean water. In modern agriculture systems however, the nutrient solutions are mostly deficient in bioavailable silicic acid and the added silicates are unable to compensate for this deficiency.

Although silicates and (poly)-silicic acid are sometimes included in formulations of nutrients, these compounds are not bioavailable enough as such, because they are not absorbed. Moreover only a low percentage of silicates and silica gel in water is slowly hydrolysed into orthosilicic and disilicic acid.

Only these small sized silicic acid compounds (mono (=ortho) and disilicic acid) are highly bioavailable and are the relevant bioactive silicon molecules for the metabolism of diatoms, plants, animals and humans.

On the other hand orthosilicic acid is a relatively unstable molecule with a tendency to polymerise into dimers, trimers, etc. (=oligomeric) molecules (non-colloidal silicic acid) and following to larger molecules of several thousands of silicon molecules being small particles of 1-8 nm, such as 1.5-6 nanometers, the micro-colloidal phase. These micro-colloidal particles aggregate into longer chains, leading to a real three-dimensional network (colloid). This process results in the formation of a soft gel, which is poorly bioavailable. The formation of these colloids and gels is pH dependent. The longest gelling time occurs at pH 2. At lower and more alkaline pH, the time for colloid and finally gel formation decreases (Iler R K. The Chemistry of Silica. Wiley: New York, 1979).

The stages from monomer to sol-gel polymerization can be summarised as follows:
1. monomer orthosilicic acid in acid medium;
2. polymerisation of orthosilicic acid, from monomers into dimers, trimers, tetramers, etc., linear or cyclic (oligomers) up to structures of more than thousand silicon molecules;
3. further condensation into linear or randomly branched polymers (small spherical particles (pre-sol/micro-colloidal, particle size between 1.5-10 nm consisting of several thousands of silicon molecules);
4. growth of these particles (sol, colloidal, particle size of about 10-100 nm);
5. linking of particles into chains (aggregation, colloidal);
6. chained into network and extension throughout the liquid (aggregation, pre-gel);
7. thickening into a gel.

It is described that silicon is absorbed via the roots as orthosilicic acid. Usually, silicates, silica gel (colloid), metasilicates, zeolites and other silicon compounds are used as silicon source, however, having a low bioavailability. To date, new data suggest that also other silicon compounds (e.g. disilicic acid) are absorbed by special membrane proteins (aquaporins).

New chemicals that are used in agriculture also induce polymerisation and aggregation of orthosilicic acid into colloids (e.g. fluorides, nitro- and chlorinated compounds, insecticides, antibiotics, fungicides etc.). By that, synergetic activity between roots and microbes, resulting in better bioavailability of minerals and solubilisation of silicates is omitted or reduced, which results in weaker plants with a lower mineral content. To circumvent this problem, plants have to get more fertilizers than necessary and also have to be protected by insecticides, fungicides, etc., more than necessary. This is especially a problem for plants on hydro culture.

In addition to the importance of silicon to plants, there is also evidence that silicon is an essential element for animals and humans (Laane, H. M.: Silicon for humans: beneficial or essential? Abstracts of 4$^{th}$ International Conference on Silicon in Agriculture, 2008; 59).

The question arises if silicon is also able to protect and strengthen animals and humans against infiltration of pathogenic microbes (bacteria, fungi) and could directly be related with certain physiological conditions. The human body contains a very substantial amount of silicon, far higher than most essential trace elements like Mn, Fe, Cu or Zn. Especially organs like connective tissue, cartilage and bones contain high amounts of silicon. Some studies show that the silicon contents decrease with age. Pregnant women have low silicon serum concentrations and the use of silicon supplements by them showed therapeutic action on the skin and lowers aluminium toxicity (Reffitt D M, Jugdaohsingh R, Thompson R P H, Powell J. J.: Silicic acid: its gastrointestinal uptake and urinary excretion in man and effects on aluminium excretion. J. Inorg. Biochem. 1999; 76:141-6; and: Van Dyck K., Van Cauwenbergh R., Robberecht H., Deelstra H.: Bioavailability of silicon from food and food supplements. Fresenius J. Anal. Chem. 199; 363:541-4). The use of silicon supplements also reduces aluminium toxicity. Aluminium inhibits bone formation and is correlated with neurological diseases like Parkinson and Alzheimer.

Silicon is connected with the elasticity of the artery and blood vessel walls and enhances the immune system.

There are clinical reports on improvement of skin diseases, heart diseases, asthma, rheumatic diseases, psoriasis, bone diseases, etc. by using silica gels. Silica gels are used all over the world. However, these gels are poorly bioavailable because of difficulties to dissolve bioavailable silicic acid.

The bioavailable form of silicon is orthosilicic acid and disilicic acid, not silica. Silica is silicon dioxide, which is not bioavailable. Silicon is found in food (and horsetail) as silicates, which are likewise not bioavailable. All dietary silicates must be transferred into orthosilicic and disilicic acid being the relevant bioavailable compounds to be absorbed and used by the body.

Orthosilicic acid, however, is unstable. In concentrations over 1 ppm (the maximum amount typically found in mineral water) orthosilicic acid readily polymerizes into long chains which are not bioavailable.

Hence, to use silicon in an effective bioavailable way, one has to use a bioavailable silicic acid solution and one has to prevent the polymerization process. However, it is very difficult to inhibit polymerization leading to gel formation in highly (>0.1% Si) concentrated solutions at all pH values.

Next, colloids and gels as such are not bioavailable. From the (macro) colloidal stage depolymerisation is very limited and hardly reproducible. This results in a very low concentration of orthosilicic acid.

Human supplementation studies reveal that solid silicon supplements such as colloidal silica and phytolytic silicates are hardly or even not at all bioavailable whereas it is proved in prior art that a solution of stabilized orthosilicic acid in a HCl-choline matrix has a high bioavailability (Calomme M., Cos P., Vingerhoets R., Van Hoorebeke C., Vanden Berghe D. (1998): Comparative bioavailability study of silicon supplements in healthy subjects, Journal of Parenteral and Enteral Nutrition, 22, S12, (abstract #47) Van Dyck K., Van Cauwenbergh R., Robberecht H., Deelstra H.

Boron has similar effects in plants, animals and humans. In animal and humans boron increases bone growth and strength, plays a role in the prevention of osteoporosis and other functions. In plants silicon and boron have mutually enhancing effects on as well plant growth as on the reduction of stress factors amongst others a lower infection rate.

An object of the present invention is to prepare a stable solution or powder of micro-colloidal silicic and boric acid from which bioavailable and bioactive silicon and boron are readily absorbed by the body and the plant.

Another object of the invention is to have a simple but innovative method to prepare the above mentioned solution or powder.

Yet another object of the present invention is to stabilize the silicic acid in the micro-colloidal phase with a particle seize around 4 nanometers (such as ±1.5-6 nm) consisting of many hundreds till few thousands of silicic acid molecules partly coupled with boron molecules to form micro-spheres (as determined from NMR-spectra) also called micro-colloidal as a precursor to easily release ortho—and disilicic acid.

$^{29}$Si NMR spectra were acquired at 298K using a Bruker DMX-400 spectrometer operating at 79.4 MHz equipped with a 10 mm BBO probe.

Data were typically acquired with a spectral with of 300 ppm in 32K data points, a relaxation delay of 10 sec and 1024 scans. As a reference external TMS was used.

Another object of the present invention is to have the prepared solution stable for at least a year and the powder stable for at least 2 years.

Yet another object of the present invention is to have the prepared solution of micro-colloidal silicic acid and boric acid in which other compounds like other minerals, vitamins, amino acids, etc. can be dissolved.

The present invention includes an aqueous solution with silicic acid and boric acid with a silicic acid particle size around 4 nm, such as especially in the range of 1-8 nm, such as 1.5 nm to 6 nm consisting of many hundreds till few thousands of silicic acid molecules coupled together to form micro-spheres (determined from NMR-spectra) also called micro-colloidal. This solution can also comprise a water absorbing additive. The solution contains bioavailable silicon and the solution may be stable for at least 1 year. Herein, the phrase "particle in the range of 1-8 nm" and similar phrases may especially indicate that at least 90% of the particles have a particle size in that range, especially at least 95%, such as substantially all particles. The particle size can for instance be determined with TEM or SEM. Especially, the silicic acid particles have particle sizes in the range of 1.5-6 nm (especially at least 90%). Even more preferably, at least 90% of the particles have a particle size in the range of 3.5-4 nm.

Hence, the invention especially provides a composition comprising an acidified aqueous solution of (1) micro colloidal silicic acid, (2) boric acid, and (3) a water absorbing additive, having a pH value of equal to or less than 1, wherein the micro colloidal silicic acid has particle sizes in the range of 1-8 nm. The invention thus provides a composition with micro colloidal silicic acid, in contrast to prior art compositions which are non-colloidal (with particle sizes below 1.5 nm).

The invention also comprises a method for the preparation of a solution in which silicon and boron and one or more other micro-nutrients compounds (like zinc, copper, molybdenum, selenium, humic acids, fulvic acids, amino acids and others) are hydrolysed in an acidic aqueous solution. This solution can contain one or more dissolved (strong) water absorbing additives (humectants). The solution can also be processed to a particulate product or powder by removing at least a part of the aqueous liquid, especially a major part.

Especially, the solution can be processed to a dry powder by removing the water of the aqueous liquid. A free flowing particulate product may be provided.

The invention especially provides a method of preparing such composition, the method comprising:
providing in a first process a first mixture of a water absorbing additive and an acidified aqueous liquid,
providing in a second process a second mixture of a silicon source and an aqueous liquid,
mixing in a mixing process, preferably at a temperature in the range of >10° C. and <35° C., preferably at a temperature in the range of 15-30° C., even more preferably 18-22° C., the first mixture and the second mixture to provide a stock solution, wherein the first mixture of water absorbing additive and acidified aqueous liquid is stored for at least 6 hours before mixing with the second mixture of silicon source and aqueous liquid, and wherein the method further comprises adding a boron source to one or more of the second mixture and the stock solution.

The first mixture preferably has a low pH, such as lower than 1, like lower than 0.5. Acidification may for instance be performed with $H_3PO_4$ and/or HCl. The second mixture may or may not be acidified.

Preferably, the first mixture is stored for at least 6 hours, even more preferably at least 12 hours, yet even more preferably at least 18 hours. This allows the water absorbing additive to saturate with water. Preferably, the first mixture is stored without substantial stirring. Further, preferably the first mixture is stored at a temperature in the range of >10° C. and <35° C., preferably at a temperature in the range of 15-30° C., even more preferably at a temperature in the range of 18-22° C.

The invention also includes the use of this solution or powder, in which, in general after dilution, the final solution (thus after the dilution, if any) is added to plants or trees, to increase its resistance against one or more of the group of microbial infections, insects, pests, fungi, weeds, or extreme physical conditions. The pH of the solution that is applied is in general in the range of 4-6.

The invention also comprises the use of the solution or powder, for use after dilution, to strengthen the seeds of plants, trees, etc.

The invention also comprises the use of the solution or powder, for use after limited dilution, as a growth retardant for plants and flowers.

The invention also comprises the use of the solution or powder (after dilution) for oral use to strengthen different types of connective tissue, bones, cartilage and joints, arteries, skin, hair and nails in humans and animals (including fish).

The invention also comprises the use of the solution or powder (after dilution, e.g. solved in creams, gels, etc.), for topical use to strengthen and improve skin, hair and nails in animals and humans.

The invention also comprises the use of the solution or powder, for use to stimulate the immune system as well in humans, animals as plants.

DESCRIPTION OF THE INVENTION

The present invention relates to a solution containing silicic acid in the micro-colloidal phase as a precursor to easily release of bioavailable and bioactive silicon, preferably combined with boron stabilized by water absorbing additives. The solution can also comprise other minerals like copper, molybdenum, selenium, zinc and/or (micro)-nutrients and/or compounds, like humic/fulvic acid, amino acids, etc.

The first aspect of the present invention relates to the preparation of a stock solution comprising silicic acid compounds with boron stabilized by water absorbing additive (humectant). Optionally one or more micro-nutrients, like for example selenium, copper, molybdenum, zinc, etc., can be added.

The second aspect of the invention is a method for preparing an aqueous solution, especially with a rotary jet mixer, including inhibiting or even stopping the polymerization reaction with humectants at acidic pH, after which boron (especially in the form of boric acid) is added. In addition one or more other micro nutrients can be added.

The third aspect is spray-drying, spray-chilling, or lyophilization like freeze-drying of the said stock solution by which the solution is transferred into a powder, containing silicic acid and boric acid (and the water absorbing additive).

It has been found that the combination of bioavailable silicon with boron is synergistic and causes an enhanced bioavailability and bioactivity of silicon.

Since the silicic acid should be present in a micro-colloidal form to be easily transformed to bioavailable silicon, formation of macro-colloidal silicic acid should be prevented. This can be done by choosing the right concentration, e.g. a concentration around 1% Si, as shown by NMR.

A combination of bioavailable silicon, boron and a strong water absorbing additive gives a solution with high concentrations of micro-colloidal silicic acid (e.g. 2 wt. % Si can be reached. Such a solution should have a low pH, below pH 1 and preferable below 0.5. This low pH can be reached by adding acids like HCl or $H_3PO_4$. Because the pH is very low (e.g. <1), water and particles are highly protonated.

Mainly micro-colloidal particles of around 4 nm (NMR) are found but generally the size may be in the range 1.5 nm to 6 nm. Because of the strong action of the humectant these micro-colloidal particles will not grow further into larger colloidal aggregates finally resulting in precipitation.

The presence of silicic acid compounds can be made visible by NMR technology and it is shown that micro-colloidal particles are formed with nanometer dimensions. Because of the presence of a stabilizer these particles do not polymerize into macro-colloids. The relation between silicon and boron in the micro-colloidal phase is not yet complete clear. In the micro-colloidal phase silicon-boron bonds (B—O—Si) were seen as shown by NMR. Hence, it seems that a silicon-boron complex may be available.

Hence, the solution of the invention, is micro-colloidal silica, i.e.: silicic acid that is (mainly) in stage 3 (polymerisation of orthosilicic acid into small particles/micro-colloid) and also the combination of this solution with a set of micro-elements or micronutrients like i.e. zinc, molybdenum, humic, amino acids and fulvic acid.

The invention is not directed to colloidal silica or silica as sols (stage 4 and higher). Colloids comprise particles of approximately 10 to 100 nm (Kirk-Othmer, 'Colloids') and Rompp describes in his Chemie Lexikon silicasol as an aqueous anionic solution of colloidal amorphous $SiO_2$, with a mean particle size of 15-150 nm.

The biological activity of the solution of the invention is due to these micro-colloidal particles with boric acid. Pure micro-colloid silicic acid has a lower activity. The humectant enables high concentration of micro-colloidal silicic acid in stage 3 and prevents aggregation. Aggregation of these particles (stage 4 and higher) results in opalescence, turbidity, light reflection, colloid and gel formation and thus loss of bioactivity.

If an additive is used, this humectant is preferably chosen out the group of food additives (E-list). Hence, the solution according to the present invention is a solution in which the water absorbing additive (humectant) may be polysorbate, a vegetable gum, a substituted cellulose, a polyglycerol ester of fatty acids, a polyethylene glycol, a polydextrose, propylene glycol, propylene glycol alginate, a polyoxy ethylene glycol ester, a pectine or amidated pectine, a sucrose ester of fatty acids, acetylated or hydroxypropyl starch, starch phosphates, urea, sorbitol, malitol, a vitamin, etc. or mixtures thereof. The strong humectant may prevent that polymerization proceeds beyond the micro-colloid stage.

To obtain a high concentration of micro-colloidal silicic acid, a high concentration of the water absorbing additive is necessary. The water absorbing additive in the solution of the invention is preferably present in a concentration of at least 30% (W/V, Weight per volume for powders and V/V for liquids), preferably at least 40% for liquids. Boron is preferably present in a concentration of around 0.2%. Such solutions can be stored as stock solution and kept for a long time (>1 year) at room temperature before dilution and application in plants, animals and humans. Hence, in this way a solution is created with a high concentration of micro-colloid silicic acid, that can be used as stock solution in which silicic acid is present in its micro-colloidal form and in presence of a set of nutrients like selenium, zinc, molybdenum e.g. The concentration of micro nutrients in the solution ranges from 0.0001 to 10% V/V. This solution has a pH below 1, preferable below 0.5.

Boric, silicic and also humic and fulvic acid (extract of humic/fulvic material and heterogeneous material, comprising organic weak acids and minerals) are weak acids and poorly soluble in water. In low concentrations they are common in non-polluted water all over the earth. They are vital for mineral health of plants, animals and humans. All these acids become depleted in polluted systems and by that, their bioavailability decreases. It has been found that selected mixtures of these acids in liquid formulations at low concentrations stimulate normal health conditions and could be used as nutrient preventing several diseases and as anti-aging agents. Hence, the solution of the present invention can also comprise in a specific embodiment humic/fulvic acid. In such a solution, humic/fulvic acid is present in a final concentration between 0.1 and 10% (V/V).

Concentrated solutions like these, comprising micro-colloidal silicic acid, boric acid, a set of (micro)-nutrients like humic acid (i.e.) and a water absorbing additive can be prepared in a way in which one or more silicon and boron compounds are hydrolysed in an acid solution containing one or more dissolved water absorbing additives. During this method, the water absorbing additive (humectant) is dissolved in acidified water.

It is preferred to acidify and to fully hydrate the water absorbing additives (humectants as liquids or with water mixed powder), preferably for at least 6 hours, such as at least 12 hours e.g. approximately a temperature >10° C. and <35° C., before adding silicates (e.g. an alkali or alkaline earth silicate solution), preferably by a special mixing process, especially with a rotary jet mixer. A good result was e.g. obtained with the mixing of an identical volume of a diluted 4-12 fold alkaline potassium silicate solution (12-18% Si) in water (water preferably has approximately a temperature >10° C. and <35° C.) which is added to the concentrated propylene glycol or PEG or other humectants. Preferably, at last boron (e.g. boric acid) is added.

The mixing may in an embodiment be done with a rotary jet mixer which may provide fast and efficient, hydraulically-balanced mixing. The liquid to be mixed is circulated from the tank via a pump to the rotary jet mixer which may be positioned under the liquid surface. The liquid flow may be used to drive a gearing system which makes the nozzles of the rotary jet mixer to rotate around both the horizontal and vertical axes. In an embodiment, the apparatus (plant) as described in WO 0224317 (which is herein incorporated by reference) may be applied for mixing the liquid.

The concentration of the humectant, in the aqueous liquid comprising the humectant that is used to form the composition of the invention, is preferably at least 80% and in the final silicon containing solution, the final humectant concentration is preferably at least 30%, such as preferably at least 40%.

After homogenization the silicic and boric acid solution and humectant solution (and optional further components such as one or more (micro) nutrients), the composition may be processed into a powder, for instance by spray-drying with a spray dryer with for instance a two-fluid nozzle with high performance cyclone. However, also other methods may be applied, such as freeze-drying, etc. The particle size in the powder thus obtained may preferably ranges from 0.1-10, especially 0.3 to 5 micrometer. This may especially indicate that at least 90% of the particles, especially at least 95%, have the particle size in that range. This may for instance be determined by SEM.

The invention also provides the composition of the aqueous solution of an additive with other compounds like micro-nutrients and the silicic and boric acid solution, before use.

This composition may be obtained after combining the starting products, such as the silicic acid solution, the boric acid solution, and the humectant containing solution.

The composition may also be obtained after dissolving the powder as described above.

After the combination, the obtained powder can be dissolved, diluted and applied. For example, the silicic and boric composition is, before use diluted and sprayed on plants. Several combinations of solutions are possible, to obtain the solution of the invention. The micro colloidal solution obtained can be stored for a longer period than one year. The micro colloidal containing powder can be stored for longer than 2 years.

Due to the low pH of the composition, in general dilution is required before use, in such a way that an acceptable pH is reached. It is preferable that the final solution after dilution has a pH range of 4 to 6. This pH will depend upon the application. The pH may, if necessary, be adjusted by adding a base, such as KOH or NaOH (preferably while mixing) or an acid.

The concentrated solution or dissolved powder according to the present invention can, after dilution, be added to plants or trees. A dilution factor of at least 100 may be required before adding to plants or trees. The diluted solution according to the present invention can be used to strengthen plants, tree and their seeds, to increase their resistance against microbial infection, insects, pests, fungi, or extreme physical conditions like heat or freezing. If the dilution factor is lower than 80 the diluted solution can be used as a safe growth retardant for plants and flowers. The pH range of 4-6 is preferably used since the uptake into plants is optimal at this pH interval.

It is clear that the (concentrated) solution or dissolved powder added to the plants or trees may also contain other additives. These additives can for example be added after dilution. The additives can also be added to the concentrated stock solution. Additives are for example, minerals, nutrients, anti-microbial agents, insecticides, pesticides, fungicides, herbicides, etc., or combinations thereof. Preferably, these additives do not substantially influence the micro-colloidal nature of the silicic acid in the solution or extend it to a real colloid formation. However, when the solution according to the invention is used (after dilution) to spray e.g. on fruit, usually the less fungicides etc. are necessary, because of the improved fruit quality and immunity.

The concentrated solution or dissolved powder of the present invention can, after dilution, be added by spraying on plants or trees and/or their leaves and/or their crops and/or seeds or by adding the solution to the medium in which the plants or trees have their roots (hydroponically use) or to the soil. In the same way the solution can be hydroponically used, after dilution, for germinating seeds.

As described above, this will enhance the health of the plants or trees. It is also a way to concentrate boron and silicon in e.g. vegetables and fruits. Vegetables and fruits can then be used for human consumption.

Good results on several crops, e.g. on fruit like bananas, apples, grapes, pears, on rice, wheat unions, potatoes, tomatoes and also on flowers etc., can e.g. be obtained with a solution that has a Si concentration of about 0.2 to 2 wt. %, a B concentration of 0.01-0.2 wt. % and as humectant in an amount of about 30 to 60, preferably about 35 to 50 wt. %. The pH of this solution is less than 1.

The (concentrated) solution of the present invention may also be used after saturation in super absorbers like polyacrylates (sodium polyacrylate or homo polyamino acid compounds like poly aspartate, or natural materials like clays or zeolites, etc). Mixtures of these compounds together with soil substrates can be used as slowly releasing agents, for example slowly releasing Si, B, Se and humic/fulvic acid, amino acids to plants.

The (concentrated) solution or dissolved powder of the present invention can also be used, after dilution, to strengthen fish (including shellfish) and to increase their resistance against microbial infection. The solution or dissolved powder will usually be diluted approximately 1000 to 30000 times, before adding to the fish. It can for example after dilution be added to the basin of the fish, such that the appropriate concentration of the acids is obtained. This solution can also be used to concentrate boron and silicon in algae.

This solution or powder can also be used in combination with minerals, nutrients, anti-microbial agents, or combinations thereof. These additives can for example be added after dilution of the concentrated solution or dissolved powder. The additives can also be added to the concentrated stock solution.

The (concentrated) solution or (dissolved) powder of the present invention can also be used, after dilution, in humans and animals to strengthen e.g. connective tissue, bones, skin, nails, arteries, cartilage and joints. Humans and animals benefit from both the bioavailable silicon and other nutrients and especially the synergetic effect of increased bioavailability of silicon by the presence of boron.

The solution or (dissolved) powder, after dilution, can be used for the treatment of diseases related with of bone, skin, arteries, connective tissue, cartilage, joints, osteoporosis, rheumatic diseases, arteriosclerosis, hair, nail and skin diseases, cardiovascular diseases, allergic diseases, arthritis, degenerative diseases, etc. The solution or powder should be used in a therapeutic form, this means including possible physiological acceptable additives. This can e.g. be done by adding drops of an undiluted or diluted solution or (dissolved) powder to drinks, using the undiluted or diluted solution or powder in the preparation of medicines foods as food additive or as supplement, and other methods. The solution or powder can also be used in cosmetics, (therapeutic) creams and ointments, shampoos, gels, etc., and in the preparation thereof The final dilution of the solution or dissolved powder should be such, that an acceptable pH is reached. This will depend upon the application. Usually, the dilution with water (or water based liquids) will range from approximately 20 to 1000 times, before intake. If necessary, the dilution can be less or more. When diluting the solution or increasing the pH of the solution, e.g. in the course of an application, it is preferred that the pH is not higher than about 4-6. When the pH is higher than about 6, the beneficial effects decrease. Hence, the solution will mainly be used at acid pH's (less than about 6). Smaller dilutions (like about <20 times) may provide less stable diluted solutions, whereas stronger diluted solutions (like about larger than 500 or 1000 times) may provide longer stable solutions for application.

Also the intake and/or the frequency of use of e.g. cosmetics comprising the (diluted) solution or powder of the present invention will depend upon the application. The total human intake per day may approximately be 0.5 to 10 mg Si for a 50 kg body weight (animals and humans) and 0.5 to 1 mg B for a 50 kg body weight; in cosmetics, the concentration may preferably approximately be 0.5 mg/ml to 0.001 mg/ml Si and 0.2 mg/ml to 0.001 mg/ml B in cosmetics.

Depending upon the application, the (concentrated) solution of the present invention the stock solution may include additional additives. The additional additives may be a flavoring agents, sweeteners, coloring agents, preservatives, stabilizing agents, etc. These additives can for example be added after dilution of the concentrated solution or powder and before use. But the additives can also be added to the concentrated stock solution. Preferably, these additives do not substantially decrease the solubility of the micro-colloidal silicic and boric acid in the solution and do not promote to (macro) colloid formation or gelling.

Hence, in summary, the invention provides a composition comprising an acidified aqueous solution of (1) micro colloidal silicic acid, (2) boric acid, and (3) a water absorbing additive, having a pH value of equal to or less than 1, wherein the micro colloidal silicic acid has particle sizes in the range of 1-8 nm, even more especially, wherein the micro colloidal silicic acid has particle sizes in the range of 1.5-6 nm.

The water absorbing additive preferably comprises a humectant selected from the group consisting of a polysorbate, a vegetable gum, a substituted cellulose, a polyglycerol ester of a fatty acid, a polyethylene glycol, a polydextrose, a propylene glycol, a propylene glycol alginate, a polyoxy ethylene glycol ester, a pectine or amidated pectine, a sucrose ester of a fatty acid, an acetylated or hydroxypropyl starch, a starch phosphate, urea, sorbitol, malitol, a vitamins, and a mixture of two or more of such humectants.

The water absorbing additive concentration is at least 30% of the composition, especially, the water absorbing additive concentration is in the range of 30-60% of the composition.

Preferably, the molar Si/B ratio is in the range of 1.5-300 (i.e. the number of moles of Si is present at least 1.5 higher than the number of moles of B).

The composition may preferably further comprise an additional additive, for instance selected from the group consisting of a flavouring agent, a sweetener, a colouring agent, a preservative and a stabilizing agent, and a combination of two or more of such additional additives, and alternatively or additionally an additional nutrient selected from the group consisting of zinc, copper, molybdenum, selenium, a humic acid, a fulvic acid, an amino acid, and a mixture of two or more of such additional nutrients.

The composition as claimed may especially have a pH value preferably equal to or less than 0.5. The composition may further comprise one or more of HCl and $H_3PO_4$.

The shelf life appears to be at least one year at room temperature.

The invention further provides a dilution of the composition as claimed as described herein having (after dilution) a pH in the range 4-6.

The invention further provides a method of preparing a composition as defined herein, comprising:
  providing in a first process a first mixture of a water absorbing additive and an acidified aqueous liquid,
  providing in a second process a second mixture of a silicon source and an aqueous liquid,
  mixing in a mixing process at a temperature in the range of >10° C. and <35° C., preferably at a temperature in the range of 18-22° C., the first mixture and the second mixture, preferably in a rotary jet mixer, to provide a stock solution, wherein the first mixture of water absorbing additive and acidified aqueous liquid is stored for at least 6 hours, preferable 12 hours, such as at least 18 hours, before (said) mixing (in said mixing process) with the second mixture of silicon source and aqueous liquid, and wherein the first mixture is stored preferably without substantial stirring, and wherein the method further comprises adding a boron source to one or more of the second mixture and the stock solution. The aqueous liquid used may especially be water, but may optionally also be a mixture of water and one or more other water miscible liquids. The ratio of the amount of such liquids relative to water is preferably at least 1:5, even more preferably at least 1:10, yet even more preferably at least 1:20 (i.e. for instance 1 liter other liquid and 20 liters water).

Especially, the silicon source is a silicate, especially an alkali silicate, even more especially potassium silicate, and wherein the boron source is boric acid.

Preferably, the first mixture is stored for at least 12 hours before mixing with the second mixture. Storage is preferably at >10° C. and <30° C. Preferably, the boron source is added after mixing the first mixture and the second mixture.

As indicated above, the storage (before the mixing process) is preferably without introducing turbulence through for instance mixing. Especially, the mixing process, which is performed after the storage of the first mixture for at least 6 hours, is performed in (with) a rotary jet mixer, such as indicated herein.

The invention further provides a method of preparing the dilution as defined herein, comprising performing the method of preparing a composition as defined herein, maintaining the composition thus obtained (i.e. after mixing the acidified aqueous liquid, the water absorbing additive, the silicon source and the boron source) for at least 6 hours at a temperature in the range of >10° C. and <35° C., especially at a temperature in the range of 18- 22° C., preferably without substantial stirring, and subsequently diluting the composition with an aqueous liquid to arrive at a pH in the range of 4-6.

Especially the aqueous liquid, the silicon source, the water absorbing additive and the strong acid may be mixed in a rotary jet mixer. In operation, the liquid in the rotary jet mixer may be circulated from the tank of the mixer via a pump to the rotary jet, which is positioned under the liquid surface. The liquid flow is used to drive a gearing system which makes the nozzles of the rotary jet rotate around one or more, and preferably both, the horizontal and vertical axes. An example of a rotary jet is described in WO 0224317, which is incorporated herein by reference. After this mixing boron as boric acid is added.

The invention further provides a method of preparing the dilution as described herein, which method may comprise performing the method of preparing a composition as defined herein, maintaining the composition thus obtained for at least 12 hours at a temperature in the range of >10° C. and <30° C., especially at a temperature in the range of 18-22° C., without substantial stirring, and subsequently diluting the composition with an aqueous liquid to arrive at a pH in the range of 4-6 because the uptake into plants is optimal at this pH interval. This dilution is stable for at least 12 hours at a temperature in the range of >10° C. and <35° C.

The invention further provides a particulate product (powder). This may for instance be obtained by executing the method of preparation as defined herein, and removing, preferably by spray-drying, the aqueous liquid and producing a particulate product.

Hence, the invention also provides a particulate product (obtainable by the method as defined herein), wherein the particles (of the particulate product) comprise (1) silicic acid, (2) boric acid, and (3) the water absorbing additive, and wherein at least 90% of the particles in the particulate product have particle sizes in the range of 0.1-10 µm, especially 0.3-5 µm. The particulate product may comprise other materials, such as micro nutrients (see also above).

The particulate product may have a shelf life of at least two years at room temperature.

The invention further provides a dilution, as defined herein, which may be obtainable by dissolving the particulate product as defined herein in an aqueous liquid and optionally adjusting the pH to a range of 4-6.

The dilution as defined herein, may be used for all kind of individual, of if desired a possible combined, applications:
  to germinate the biological characteristics of seeds;
  to enhance the biological characteristics of seeds;
  to strengthen a plant, a tree, or a crop, or their seed;
  to increase the resistance of a plant, a tree, or a crop, or their seed, against one or more of the group of a microbial infection, an insect, a pest, a fungus, or an extreme physical condition;
  with a dilution factor lower than 80, especially lower than 50, for use as a safe growth retardant to slow down the growth of plants and flowers especially in the end phases of the growth and flowering;
  to strengthen fish and to increase their resistance against microbial infection.

The invention further provides a dilution as defined herein for strengthening one or more of the group of connective tissue, bones, skin, nails, arteries, cartilage and joints.

The invention further provides a dilution as defined herein, for use in the treatment of diseases related with one or more of the group of bone, skin, arteries, connective tissue, cartilage, joints, osteoporosis, rheumatic diseases, arthritis, arteriosclerosis, hair, nail and skin diseases, cardiovascular diseases, allergic diseases, degenerative diseases and immune diseases.

The composition defined herein or the dilution as defined herein, may be used:
  in a therapeutic form;
  as food additive or food supplement;

in a cosmetic, a therapeutic cream, an ointment, a shampoo or a gel for a human or an animal;

in combination with another substance, in a cream, an ointment or a gel ('coatings') for a plant, a tree or a crop.

EXAMPLES

Experiment 1: Preparation of stock solutions; test of the stability in time.

Concentrated liquid sodium and potassium silicates were used as starting materials (13% WN Si as silicate). Concentrated solutions were first five to tenfold diluted in different concentrated humectants acidified until pH 0.5. These stock solutions contained up to 1% Silicon and up to 0.2% Boron. Only addition of highly concentrated humectants such as non-toxic food additives like polysorbates, polyethylene glycols, propylene glycol, urea, polydextrose, sorbitol, etc. resulted in stable solutions of both acids.

All these humectants are highly mixable with water and also mixable with different kinds of silicates or silanols. Only strong humectants (e.g. those that absorb water about 0.5 times or stronger water than glycerol) were able to inhibit colloid formation beyond micro-colloid stage of silicic acid after long time.

The stability in time for different strong humectants and their combinations was observed during 32 weeks at 50° C.

It was concluded that the humectant concentration must be at least 30%, preferably 40%, in the final acidified stock solution to inhibit colloid formation beyond the micro-colloid stage.

Examples of such strong absorbing additives are propylene glycol, PEG 200, 400, 600 and 800, urea, dextrose, polysorbate, sorbitol, galactose, cellulose, dextran, vegetable gum, and combinations thereof. Lower concentrations than 30% WN resulted in extended colloid and gel formation after 3 months or even earlier in some cases.

Biological Test of Type Humectants:

Experiment 2: Preparation of stock solutions: search of for a good stabilization of the active particles (micro-colloidal) and of the biological activity.

In order to use economically the synergetic effect, two plants were selected as antifungal model: Lollo Bionda (a salad) and White Lisbon (an onion). In both cultures strong antifungal compounds are used to inhibit fungal infection (Botrytis), resulting in leaf blight. Plants are cultivated outside during March-August, completely without Botrytis after treatment with antifungal drugs. No treatment results in heavy infection.

Next the antifungal treatment (once a week spray) was replaced by several diluted stock solutions.

PEG 400 and propylene glycol (Merck) at 40% final concentration (V/V) and were used as type humectant and different concentrations silicic acid—boric acid, Si 6 mg/ml; Si/B ranged from 1/1 to 1/300, were prepared for use on the two types of plants. The stock solution was 500 times diluted before use. The best results for preventive antifungal activity and increased plant growth was silicon/boron >1.5. The ratio could even be extended up to 1:300 without losing big biological activity.

Experiment 3: Preparation of stock solution (to be diluted before use).

5 liter PEG 400 or Propylene glycol (Merck) is brought at a temperature of >18° C. and 300 ml concentrated HCL (first diluted with 300 ml aqua dest.) is added. This solution is brought at >15° C. and <30° C., and kept at this temperature for at least 12 h. Next solved 500 ml concentrated potassium silicate solution, diluted in 4.5 liters aqua dest. is added by using a special mixing technique (with rotary jet mixer). Then, 2 gram boric acid (crystalline) is added. The resulting solution contains 0.8% Si and 0.2% B and the final pH is +/−0.4.

Quality control: micro-colloidal solutions of silicic and boric acid with NMR.

The solution must be stable even 1 year after the preparation, incubated at room temperature. In order to fulfill this condition, the solution must be completely clear (transparent), show no opalescence or have color, show no effect in a turbid meter (light reflection) and should filterable without flow reduction on a 0.1 micron filter after three months at 50° C. Fivefold dilutions of the stock solution in a phosphate buffer pH 6.5 results in complete gel formation after 10 minutes, showing that a too high pH immediately results in gel formation. The solution is only partially retained in a molecular filter with cut off 5000 after 1/10 dilution, in preparations with PEG 400 or propylene glycol).

Experiment 4: Preparation of the stabilized powder; test of stability in time 1 liter of the stock solution (see example 3) with silicic and boric acid is spray-dried with a spray dryer. The particle size in the powder ranges from 0.3 to 5 micrometer. The drying gas of the spray dryer enters in laminar flow through a two-fluid nozzle 0.7/1.4 mm from the top into the drying chamber. The drying chamber is heated up with an inlet temperature of 220° C. and an outlet temperature of 95° C. The piezodriven spray head generates ultra-fine droplets, which are gently dried into solid particles. The gas spray flow is 70 mm and aspiration 100% with the peristaltic pump at 20%. The dried particles are electrostatically charged and collected at the collecting electrode.

The particle size is determined with a SEM TM-100 to be between 0.3 to 5 micrometer.

The stability in time is at least two years.

Experiment 5: Test with patients in Amsterdam (the Netherlands).

100 volunteers were evaluated. They received (in a small 25 ml plastic vial) made with PEG 400 (see above) a stock solution with micro-colloidal silicic acid (silicon=4 mg/0.5 cc daily) and boric acid (boron=0.8 mg/0.5 cc daily).

Each patient took every day and during 3 months 10 drops (=0.5 cc) solved in 150 ml. water to evaluate biological effects.

Evaluation of the biological activity was done on day 31 and 95 after starting the treatment.

Conclusion after 3 months:

- (significant) improvement of the skin and wrinkles
- improvement of brittleness of hair/stronger hairs
- significant decrease of hair loss and increase in hair growth
- improvement of brittle nails hair /stronger nails
- improvement of arthralgia (joint pain) and back pain
- boost in general wellbeing/boost of immunity/vitality
- improvement of skin disorders like psoriasis and eczema
- improvement of arthritis (rheumatoid arthritis and psoriatic arthritis)
- improvement of wound healing (ulcus cruris)
- lowering of infection rate of URI's (upper respiratory tract infections)
- improvement of allergy like hay fever and food allergy
- antihypertensive effects,
- improvement of constipation
- improvement of insomnia
- improved sexual potency
- improved fracture healing Only 4 of the 100 patients reported no effects at all.

These results show that a short oral treatment with this formulation promoted direct biological effects in patients and also that this silicon/boron compound is highly bioavailable in humans.

Experiment 6: Influence of micro-colloidal silicon/low dose boron improves the strength of hooves in horses.

During 6 months the stock solution (with silicon (4 mg/0.5 cc) and boron (0.8 mg/0.5 cc per 60 kg weight) was given daily to 12 horses, with the stock solution being sprayed on the food or diluted in the drinking water. After 6 months significant strengthening was observed on the hooves of the horses.

Experiment 7: Application of micro-colloidal silicon/low dose boron on apples (Elstar, Cox and Jonagold)

The solution, containing about 0.4 wt. % Si, about 0.1 wt. % B and about 45 wt. % PEG 400, having a pH of about 0.5, was about 800 x times diluted before use and applied to Elstar, Cox and Jonagold Fruit (apples). The fruit was treated each 2 weeks till harvesting( each time 350 ml. of the solution per ha.). It appears that after harvesting the fruit size, weight, firmness, color, TSS value (total soluble solids) and the amount of starch was in all cases higher than untreated fruit. Also the shell life time was doubled due to the hardening of the skin with 0.5-1 point.

Experiment 10: Increasing the rate of germination of the seeds of wheat

Different levels of silicic acid were tested on seeds and in pot experiments to assess their effects on improvement of seed and the growth and yield in wheat.

The findings of this study showed that when silicic acid was applied at 0.25-0.50% level, the rate of germination was increased.

Next, the silicic acid concentrations affected crop positively as all the varieties of wheat produced highest plant growth and yield at 0.25% and 0.50% silicic acid application.

Experiment 13: Growth retardant Effects by application of micro-colloidal silicon/low dose boron on rice The rice was treated with high dose microcolloidal silicon/boron foliar. The dilution factor of the stock solution, see experiments 1 or 3, was 50. The production of the Si treated plants was retarded compared to control plants.

Experiment 14: Further example of preparing a stock solution

To demi water 32% HCl is to obtain a dilution Factor DF of 0.3. Then, PEG 400 or Propylene glycol (Merck) is added to the diluted HCL solution. The solution has to stabilize for one day.

Potassiumsilicate is dissolved in demi water.

With a jet rotary mixer the potassium silicate solution is added to and almost momentaneously homogenized with the PEG solution preventing polymerization proceeding beyond the micro colloidal stage. The resulting pre-stock solution contains 0.8 w/v% Si; pH is <0.5.

Boric acid (which in itself has a stabilizing effect), is dissolved in the said pre-stock solution resulting in the final stock solution. The stock solution has to stabilize for one day.

The final stock solution contains 0.8% Si, 0.2% B and the final pH is +/−0.4.

Comparative experiment: mixing conditions

Instead of adding a mixture of water and potassium silicate, the potassium silicate was directly added to a mixture of water and water absorbing additive. It appeared that undesired polymerisation took place and a gel was obtained.

Instead of mixing a first mixture of acidified water and the water absorbing additive (here PEG) that has been stored for at least 6 hours with the second mixture, potassium silicate, silicic acid, HCl, water and boric acid are all mixed in one step. Again, it appeared that undesired polymerisation took place, and a gel was obtained.

As such the invention has successfully attempted to achieve a preparation containing bioavailable and bioactive silicon.

The description given above is only explanatory and is not limiting. The application shall cover the scope of content of subject matter that will be well understood by skilled person in the art.

The invention claimed is:

1. An acidified aqueous solution composition having a pH less than 1, comprising:
   (i) micro colloidal silicic acid particles ranging in size from 3.5 nm to 8 nm,
   (ii) one or more nutrients selected from the group consisting of zinc, copper, molybdenum, selenium, a humic acid, a fulvic acid, an amino acid, and
   (iii) a water absorbing additive for at least 30% V/V of the composition.

2. The composition according to claim 1, wherein the micro colloidal silicic acid has particle sizes in the range of about 3.5 nm to about 6 nm.

3. The composition according to claim 1, wherein the water absorbing additive comprises a humectant selected from the group consisting of a polysorbate, a vegetable gum, a substituted cellulose, a polyglycerol ester of a fatty acid, a polyethylene glycol, a polydextrose, a propylene glycol, a propylene glycol alginate, a polyoxy ethylene glycol ester, a pectine or amidated pectine, a sucrose ester of a fatty acid, an acetylated or hydroxypropyl starch, a starch phosphate, urea, sorbitol, malitol, a vitamins, and a mixture of two or more of such humectants.

4. The composition according to claim 1, wherein the water absorbing additive concentration is in the range of about 30% V/V to about 60% V/V of the composition.

5. The composition according to claim 1, further comprising an additional additive selected from the group consisting of a flavoring agent, a sweetener, a coloring agent, a preservative and a stabilizing agent, and a combination of two or more of such additional additives.

6. The composition according to claim 1, having a pH value equal to or less than about 0.5.

7. The composition according to claim 1, further comprising one or more of HCl and $H_3PO_4$.

8. The composition according to claim 1, having a shelf life of at least about one year at room temperature.

* * * * *